United States Patent
Jacksier et al.

(10) Patent No.: US 11,920,732 B2
(45) Date of Patent: Mar. 5, 2024

(54) USE OF STABLE ISOTOPES OF $CO_2$ TO VALIDATE CYLINDER PREPARATION

(71) Applicants: Airgas, Inc., Radnor, PA (US); American Air Liquide, Inc., Fremont, CA (US); L'Air Liquide, Société Anonyme pour l'Etude et l'Exploitation des Procédés Georges Claude, Paris (FR)

(72) Inventors: Tracey Jacksier, Landenberg, PA (US); Mani C. Matthew, Neshanic Station, NJ (US); Richard A. Socki, Newark, DE (US); Jun Sonobe, Yokosuka (JP); Megumi Isaji, Yokosuka (JP); James McHale, Northampton, PA (US)

(73) Assignees: Airgas, Inc., Radnor, PA (US); America Air Liquide, Inc., Fremont, CA (US); L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 1039 days.

(21) Appl. No.: 16/806,427

(22) Filed: Mar. 2, 2020

(65) Prior Publication Data
US 2021/0054970 A1      Feb. 25, 2021

Related U.S. Application Data

(60) Provisional application No. 62/890,677, filed on Aug. 23, 2019.

(51) Int. Cl.
*F17C 5/06*       (2006.01)
*F17C 7/00*       (2006.01)
(Continued)

(52) U.S. Cl.
CPC ............... *F17C 13/02* (2013.01); *F17C 5/06* (2013.01); *F17C 7/00* (2013.01); *G01N 15/08* (2013.01);
(Continued)

(58) Field of Classification Search
CPC ...... F17C 5/06; F17C 7/00; F17C 2203/0639; F17C 2203/0646; F17C 2250/0447; G01N 33/0004; G01N 2033/0096
See application file for complete search history.

(56) References Cited

U.S. PATENT DOCUMENTS 6,831,271 B1 * 12/2004 Guevremont ......... H01J 49/004
                                                      250/281
7,156,225 B2    1/2007 Jacksier et al.
(Continued)

OTHER PUBLICATIONS

Benesch, R. et al., The stability of 100 ppb hydrogen sulfide standards, Anal. Chem. 2004, 76, 7396-7399.
(Continued)

*Primary Examiner* — Eric S. McCall
(74) *Attorney, Agent, or Firm* — Elwood L. Haynes

(57) ABSTRACT

A quality control method for the preparation of dry compressed gas cylinder including passivating and/or preparing the compressed gas cylinder with the technique to be validated, filling the passivated/prepared compressed gas cylinder with gaseous carbon dioxide to a normal working pressure, wherein the gaseous carbon dioxide has a known $\delta^{18}O$ isotope ratio, maintaining the pressurized gas cylinder at ambient temperature for a first predetermined period of time, and gradually emptying the pressurized gas cylinder, while simultaneously measuring the $\delta^{18}O$ isotopic ratio, wherein a predetermined variation in the measured isotopic ratio of $\delta^{18}O$ indicates a properly prepared cylinder.

14 Claims, 2 Drawing Sheets

(51) Int. Cl.
    *F17C 13/02*     (2006.01)
    *G01N 15/08*    (2006.01)
    *G01N 33/00*    (2006.01)

(52) U.S. Cl.
    CPC .. *G01N 33/0004* (2013.01); *F17C 2201/0104* (2013.01); *F17C 2203/0639* (2013.01); *F17C 2203/0646* (2013.01); *F17C 2221/013* (2013.01); *F17C 2250/0447* (2013.01); *G01N 2015/0866* (2013.01); *G01N 2033/0096* (2013.01)

(56) References Cited

U.S. PATENT DOCUMENTS

| | | |
|---|---|---|
| 7,229,667 B2 | 6/2007 | Jacksier et al. |
| 7,794,841 B2 | 9/2010 | Benesch et al. |
| 7,799,150 B2 | 9/2010 | Jacksier et al. |
| 7,832,550 B2 | 11/2010 | Jacksier et al. |
| 7,837,806 B2 | 11/2010 | Benesch et al. |
| 7,850,790 B2 | 12/2010 | Jacksier et al. |
| 8,288,161 B2 | 10/2012 | Benesch et al. |
| 2005/0082473 A1* | 4/2005 | Socki ............ H01J 49/0468 250/288 |

OTHER PUBLICATIONS

Cole, D.R. et al., Rates and mechanisms of isotopic exchange, Reviews in Mineralogy and Geochemistry, 2001, 43(1), 83-223.
Li, Y.-E. et al., The behavior of moisture in high pressure inert cylinder gases, Vacuum, 1993, vol. 44, Nos. 5-7, 433-434.
Meier-Augenstein, W. et al., A guide for proper utilisation of stable isotope reference materials, Isotopes in Environmental and Health Studies, 2019, vol. 55, No. 2, 113-128.
Moore, J.C. et al., Development and application of a database of food ingredient fraud and economically motivated adulteration from 1980 to 2010, Journal of Food Science, vol. 77, Nr. 4, 2012.
Verkouteren, R.M. et al., Value assignment and uncertainty estimation of selected light stable isotope reference materials: RMs 8543-8545, RMs 8562-8564, and RM 8566, National Institute of Standards and Technology, U.S. Dept. of Commerce, Special Publication 2004 Edition 260-149, 1-56.

\* cited by examiner

USE OF STABLE ISOTOPES OF $CO_2$ TO VALIDATE CYLINDER PREPARATION

CROSS REFERENCE TO RELATED APPLICATIONS

This application claims the benefit of priority under 35 U.S.C. § 119 (a) and (b) to U.S. Provisional Patent Application No. 62/890,677, filed Aug. 23, 2019, the entire contents of which are incorporated herein by reference.

BACKGROUND

Stable Isotopes have been an integral part of the toolbox of many branches of science and technology. The use of Stable Isotopes in fields such as Food Authentication and Environmental research has been steadily increasing. At the heart of the toolbox is the requirement for stable calibration mixtures used for analyzer calibration. Analyzers are calibrated to increase confidence in measured analytical results, validating the accuracy, precision and reliability of the measurements. The ultimate objective of calibration is to minimize the uncertainty of the specific measurement by ensuring the accuracy of the analyzer.

Traditional mixtures in compressed gas cylinders focus on the molecular concentrations of the various components in the mixture. The stability of those mixtures is a statement of how long the concentrations of the various components will remain stable without a statistical change in concentration (as stated by the manufacturer). Some factors that influence mixture stability include:

Selection of optimum cylinder and valve materials to eliminate reactivity of the gas components with those of the cylinder package (cylinder and valve)

Utilization of appropriate internal cylinder/valve passivation treatments to enhance the inertness of the cylinder package and prevent/minimize adsorption/absorption of the gaseous components with the cylinder package Utilization of appropriate cylinder preparation techniques prior to cylinder filling, such as vacuum baking and purging to remove traces of moisture and oxygen which can interfere with the stability of the mixture It is important to note that all three of these points are critical to ensure mixture stability.

Stable isotope mixtures used for calibration of analytical equipment have an added degree of complexity: The isotopic concentration in addition to the molecular concentration must remain stable. Either or both of these may change with inappropriate cylinder preparation methods. For the analysis of stable isotopic ratios, this has been traditionally accomplished with the use of inorganic compounds as reference materials. The use of gases as calibration standards has been avoided as there is a belief that they are not stable and change as a function of cylinder pressure.

Carbon has two stable, naturally occurring isotopes with varying abundances. Although carbon has a third naturally occurring isotope, $^{14}C$, it is not stable, but radioactive. Oxygen has three naturally occurring stable isotopes as illustrated in Table 1.

TABLE 1

| Element | Isotope | Relative Abundance (%) | Protons | Neutrons |
|---|---|---|---|---|
| C | 12 | 98.9 | 6 | 6 |
| C | 13 | 1.1 | 6 | 7 |

TABLE 1-continued

| Element | Isotope | Relative Abundance (%) | Protons | Neutrons |
|---|---|---|---|---|
| O | 16 | 99.76 | 8 | 8 |
| O | 17 | 0.04 | 8 | 9 |
| O | 18 | 0.2 | 8 | 10 |

It is known that the oxygen in $CO_2$ and the oxygen in water ($H_2O$) can undergo exchange reactions using the general formula below:

$$BX^* \leftrightarrow AX^* + BX$$

Applying this more specifically to $CO_2$:

$$C^{16}O^{18}O + H_2{}^{16}O \leftrightarrow C^{16}O^{16}O + H_2{}^{18}O$$

The exchange rate increases with both temperature and pressure. Therefore, any residual moisture residing in a compressed gas cylinder can participate in this exchange reaction altering the isotopic composition of both the residual moisture and the $CO_2$.

SUMMARY

A quality control method for the preparation of dry compressed gas cylinder including passivating and/or preparing the compressed gas cylinder with the technique to be validated, filling the passivated/prepared compressed gas cylinder with gaseous carbon dioxide to a normal working pressure, wherein the gaseous carbon dioxide has a known $\delta^{18}O$ isotope ratio, maintaining the pressurized gas cylinder at ambient temperature for a first predetermined period of time, and gradually emptying the pressurized gas cylinder, while simultaneously measuring the $\delta^{18}O$ isotopic ratio, wherein a predetermined variation in the measured isotopic ratio of $\delta^{18}O$ indicates a properly prepared cylinder.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DETAILED DESCRIPTION OF PREFERRED EMBODIMENTS

A quality control method of validating cylinder preparation of compressed gas cylinders suitable to provide stability of isotopically prepared gas mixtures is proposed. The quality control method could also be advantageously used to validate cylinders for use in the storage of corrosive and/or reactive gas mixtures, since such mixtures are very sensitive to trace moisture.

The ability of $CO_2$ and $H_2O$ to undergo an exchange reaction in a compressed gas cylinder was validated by adding a known quantity of $^{18}O$ enriched $H_2O$ (at 98+% atom purity to a compressed gas cylinder, which was processed using a cylinder prep protocol via a syringe).

CO2 may be derived from many sources such as natural—limestone, combustion-based: bio-mass-derived stock, geo-fuels etc. Herein, this "class" is defined as having CO2 with isotope ratios within the natural abundance spectrum. This covers a fairly wide range. For example, where "heavy water" is used to cause species to exchange with the CO2 from the natural abundance source yields CO2 that has isotope ratios that are manipulated. These CO$_2$'s may be used as test material to determine the quality of cylinder prep.

A sufficient quantity of gaseous CO$_2$, whose isotopic values were known, was then added to the cylinder. The cylinder was then inverted/agitated several times to ensure complete mixing. After a set number of hours of heating at a prescribed temperature, the cylinder was left to sit at room temperature for a period exceeding 75 days. To stop any further isotopic exchange, the CO$_2$ was passed through a H$_2$O getter (VICI model #T100-2). The dried CO$_2$ was then transfilled into a specially prepared cylinder. The isotopic values were then measured. The change in isotopic values can be seen in Table two, which clearly demonstrates the change of $^{18}$O isotopic values.

$\delta^{18}$O—CO$_2$ Values Before and after Isotopic Exchange

TABLE 2

| | Starting value | Value after exchange |
|---|---|---|
| $\delta^{18}$O—CO$_2$ signature | −23.16‰ vs VPDB | +109‰ vs VPDB |

Trace moisture is known to desorb from cylinder walls below approximately 3 bar (~45 psi), therefore if there is residual moisture remaining in the compressed gas cylinder the CO$_2$ isotope ratios will change as the cylinder is depleted.

Figure 1:
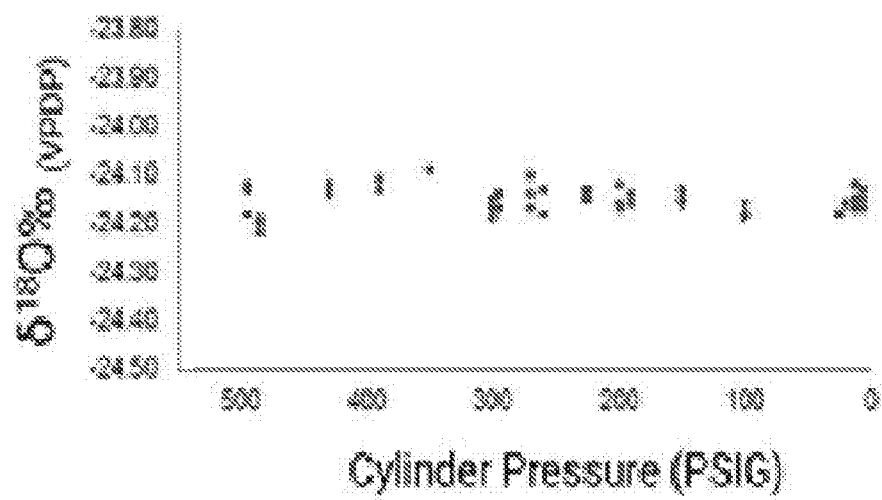
FIG. 1 illustrates the $\delta^{18}O$ ratio remaining constant over the entire cylinder contents.
Figure 2:
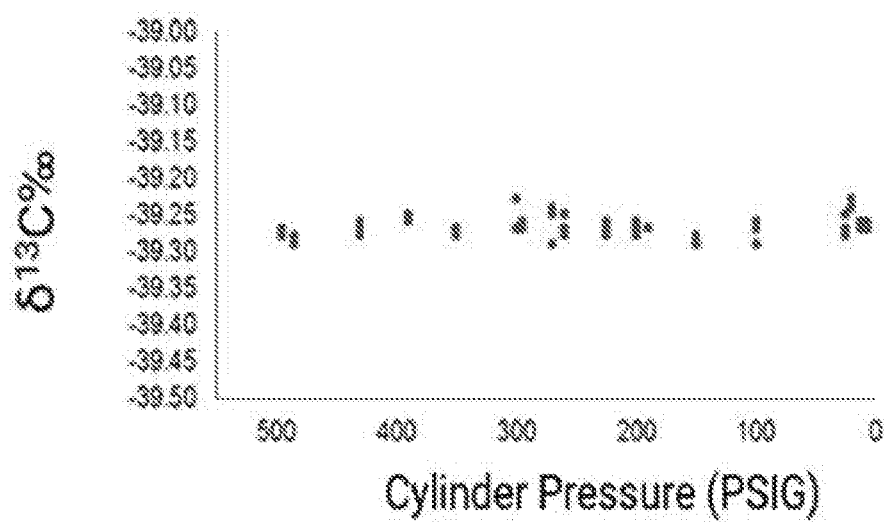
FIG. 2 illustrates the $\delta^{13}C$ ratio remaining constant over the entire cylinder contents.

As a non-limiting example, a cylinder was prepared using appropriate cylinder preparation, filled to 34 bar (~500 psi) with gaseous CO$_2$. The $^{18}$O and $^{13}$C isotope ratios were measured vs. VPDP as the cylinder was depleted at a rate of approximately 50 mL/min. FIG. 1 illustrates that the $\delta^{13}$C and $\delta^{18}$O ratios remained constant over the entire cylinder contents validating the absence of residual moisture in the cylinder.

Figure 3:
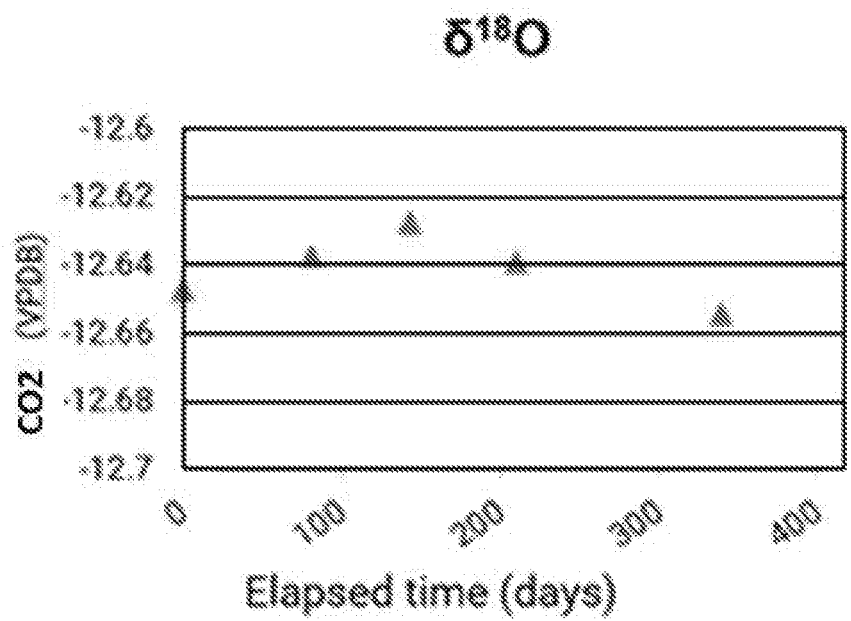
FIG. 3 illustrates the stability of a pure $CO_2$ containing compressed gas cylinder over a 1 year period, and FIG. 4 also illustrates the stability of a pure $CO_2$ containing compressed gas cylinder over a 1 year period.
Figure 4:
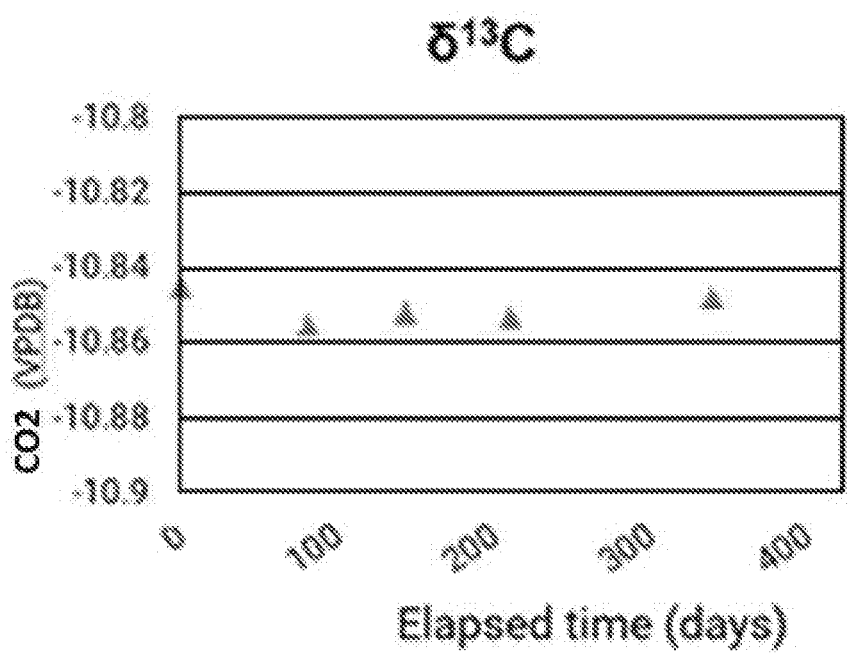

Further verification of the absence of residual moisture in the cylinder can be illustrated by measuring the stability of the CO$_2$ isotopic concentration over an extended period. The stability of a pure CO2 containing compressed gas cylinder over a 1 year period is indicated in FIG. 3 and FIG. 4.

In one embodiment, a quality control method for the preparation of dry compressed gas cylinder is provided. The first step of this method is passivating and/or preparing the compressed gas cylinder to be validated. This may be any method known in the art.

In one non-limiting example, the passivation may comprise lining the cylinder with the reaction product of a silicon-containing material and an oxygen-containing material and an amount of the reactive gas adsorbed on the reaction product. The silicon-containing material may be selected from the group consisting of compounds within the general formula (II): SiR$^1$R$^2$R$^3$R$^4$ (II) wherein R$^1$, R$^2$, R$^3$, and R$^4$ are the same or different and are independently selected from the group consisting of hydrogen, halogen, amine, alkyl, aryl, halogenated alkyl, and halogenated aryl. The silicon-containing material may be selected from the group consisting of silane, methylsilane, dimethylsilane, trimethylsilane, tetramethylsilane, and mixtures thereof. The oxygen-containing compound may be selected from the group consisting of moisture, molecular oxygen, metal oxides, and mixtures thereof. Passivation of this type is fully described in U.S. Pat. Nos. 7,156,225, 7,229,667, 7,794,841, 7,799,150, 7,832,550, 7,837,806, 7,850,790, and 8,288,161 the entire disclosure of which are incorporated herein by reference.

In another non-limiting example, the passivation may comprise heating the cylinder to a desiccating temperature while being exposed to a vacuum for a defined period of time. The desiccating temperature may be less than 70 C. The vacuum may be less than 20 microns, preferably less than 10 microns. The defined period of time may be less than 24 hours, preferably less than 15 hours. The defined period of time may be more than 6 hours.

The next step of this method is filling the passivated/prepared compressed gas cylinder with gaseous carbon dioxide to a normal working pressure. The gaseous carbon dioxide to be used will have been tested and will have a known $\delta^{18}$O isotope ratio. The $\delta^{18}$O isotope ratio may be that which is naturally occurring, that is to say within the natural abundance spectrum. Sources of such carbon dioxide may be limestone caves. Such carbon dioxide may also be derived from combustion of hydrocarbons, biomass derived sources, etc. The $\delta^{18}$O isotope ratio may also be manipulated and customized. One non-limiting example would be where "heavy water" is used to cause species to exchange with the CO2 from the natural abundance source yields CO2 that has isotope ratios that are manipulated.

The pressurized gas cylinder is then maintained at a first temperature, typically ambient temperature, for a first predetermined period of time. This first predetermined period of time may be 100 days or less. This first predetermined period of time may be 75 days or more. This first predetermined period of time may be between 6 hours and 100 days. This first predetermined period of time may be between 2 days and 75 days. The first predetermined period of time may be less than 1 day.

After this first predetermined period of time, the pressurized gas cylinder is gradually emptied, while simultaneously measuring the $\delta^{18}$O isotopic ratio. From this measurement, a predetermined variation in the measured isotopic ratio of $\delta^{18}$O is determined. It is this variation that may indicate a properly prepared cylinder.

If the predetermined variation in the measured isotopic ratio of $\delta^{18}$O reveals a standard deviation of less than 0.5‰, this may indicate a properly prepared cylinder. If the predetermined variation in the measured isotopic ratio of $\delta^{18}$O reveals a standard deviation of less than 0.1‰, this may indicate a properly prepared cylinder. If the predetermined variation in the measured isotopic ratio of $\delta^{18}$O reveals a standard deviation of less than 0.05‰, this may indicate a properly prepared cylinder.

In some embodiments, additional steps may also be performed. During the step of maintaining the pressurized gas cylinder at the first (i.e. ambient) temperature for a first predetermined period of time, the cylinder may be inverted and/or agitated, in order to endure more complete mixing.

During the step of maintaining the pressurized gas cylinder at the first (i.e. ambient) temperature for a first predetermined period of time, the cylinder may be heated for a second predetermined period of time, at a second predetermined temperature which may be based on the metallurgy of the cylinder. The second predetermined temperature may be less than 177 C for an aluminum cylinder. The second predetermined temperature may be less than 260 C for a steel cylinder.

The second predetermined temperature may be dependent on valve components, such as the seat material for the valve or the safety relief device. The safety relief device may be a fusible alloy plug or a rupture disc. Such safety devices are mandatory in North America. Therefore, in instances where the entire cylinder is contained within the oven, the second predetermined temperature may be less than 70 C. This second predetermined period of time may be greater than 20 minutes. This second predetermined period of time may be greater than 5 hours. This second predetermined period of time may be between 2 days and 60 days.

Once the preparation of a cylinder has been thus validated, isotopically prepared mixtures may be stored in this cylinder. The isotopically prepared mixture thus stored, may be a calibration mixture which then may then be used for the purpose of calibrating an analyzer. Once the preparation of a cylinder has been thus validated corrosive gas mixtures and/or reactive gas mixtures may be stored in this cylinder.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A quality control method for preparing a dry compressed gas cylinder comprising:
    a) preparing the compressed gas cylinder with the technique to be validated,
    b) filling the prepared compressed gas cylinder with gaseous carbon dioxide to a normal working pressure, wherein the gaseous carbon dioxide has a known $\delta^{18}O$ isotope ratio,
    c) maintaining the compressed gas cylinder at a first temperature for a first predetermined period of time,
    d) gradually emptying the compressed gas cylinder, while simultaneously measuring the $\delta^{18}O$ isotopic ratio, wherein a predetermined variation in the measured isotopic ratio of $\delta^{18}O$ of a standard deviation of less than 0.1‰, indicates a properly prepared cylinder.

2. The quality control method of claim 1, wherein the gaseous carbon dioxide has a natural $\delta^{18}O$ isotope ratio.

3. The quality control method of claim 1, wherein the first predetermined period of time is between 6 hours and 100 days.

4. The quality control method of claim 1, wherein the first predetermined period of time is 75 days or greater.

5. The quality control method of claim 1, further comprising:
    c1) inverting and/or agitating the cylinder, thereby ensuring complete mixing.

6. Storing isotopically prepared mixtures in a prepared compressed gas cylinder validated by the quality control method of claim 1.

7. Storing corrosive gas mixtures in a prepared compressed gas cylinder validated by the quality control method of claim 1.

8. The method of claim 1, wherein the compressed gas cylinder internal preparation comprises simultaneously exposing the cylinder to a desiccating temperature and a vacuum for a defined period of time.

9. The method of claim 8, wherein the vacuum is less than 20 microns.

10. The quality control method of claim 1, further comprising:
    c2) heating the cylinder for a second predetermined period of time, at a second predetermined temperature based on the metallurgy of the cylinder.

11. The quality control method of claim 10, wherein the second predetermined temperature is less than 177 C, for an aluminum cylinder.

12. The quality control method of claim 10, wherein the second predetermined temperature is less than 260 C, for a steel cylinder.

13. The quality control method of claim 7, wherein the second predetermined period of time is between 2 days and 60 days.

14. The quality control method of claim 10, wherein the second predetermined period of time is greater than 5 hours.

* * * * *